United States Patent [19]

Balint, Jr. et al.

[11] Patent Number: 5,037,649

[45] Date of Patent: * Aug. 6, 1991

[54] METHOD FOR TREATMENT OF HIV-INFECTED PATIENTS

[75] Inventors: Joseph P. Balint, Jr., Seattle; Frank R. Jones, Edmonds, both of Wash.

[73] Assignee: IMRE Corporation, Seattle, Wash.

[*] Notice: The portion of the term of this patent subsequent to Jan. 31, 2006 has been disclaimed.

[21] Appl. No.: 301,214

[22] Filed: Jan. 24, 1989

Related U.S. Application Data

[63] Continuation-in-part of Ser. No. 948,268, Dec. 31, 1986, Pat. No. 4,801,449, which is a continuation-in-part of Ser. No. 690,781, Jan. 11, 1985, Pat. No. 4,681,870.

[51] Int. Cl.$^5$ ............... B01D 15/08; G01N 33/543; G01N 33/552
[52] U.S. Cl. ............... 424/85.8; 424/88; 436/523; 436/527; 210/656; 210/691; 210/263; 530/413; 502/403
[58] Field of Search ............ 424/85.8, 88; 436/518, 436/523, 527; 210/656, 927, 263, 691; 530/413; 502/403; 128/DIG. 3

[56] References Cited

U.S. PATENT DOCUMENTS 4,681,870  7/1987  Balint, Jr. et al. ............... 210/691
4,801,449  1/1989  Balint, Jr. et al. ............... 424/88

OTHER PUBLICATIONS

Bansal et al., (1978) Cancer 42:1-18.
Terman et al., (1981) N. Engl. J. Med. 305:1195-1200.
Jones et al., (1980) Cancer 46:675-684.
Ray et al., (1980) Cancer 46:675-684.
Besa et al., (1981) Am. J. Med. 71:1035-1040.
Holohan et al., (1982) Cancer Res. 42:3663-3668.
Messerschmidt et al., (1982) Cancer Treat. Rep. 66:2027-2031.
MacKintosh et al., (1983). West. J. Med. 139:36-40.
Snyder et al., (1982) J. Immunol. 128:2726-2730.
Jones et al., (1984) J. Biol. Resp. Mod. 3:286-292.
Messerschmidt et al., (1988) J. Clin. Oncol. 6:203-212.
Korec et al., (1984) J. Biol. Resp. Mod. 3:330-335.
Korec et al., (1986) Clin. Oncology 4:210-215.
Nilsson et al., (1981) Blood 58:38-44.
Kiprov et al., (1984) J. Biol. Resp. Med. 3:341-346.
Kiprov et al., (1986) J. Clin. Apheresis 3:133-139.
Mehta et al., (1986) Clin. Res. 34:501A.
Snyder et al., (1987) Artif. Organs 11:334.
Snyder et al., (1988) Proc. IVth. International Conference on AIDS 1:194.

*Primary Examiner*—Nathan M. Nutter
*Attorney, Agent, or Firm*—Townsend and Townsend

[57] ABSTRACT

Patients suffering from HIV-1 infection, including both those who have and those who have not developed acquired immunodeficiency syndrome, are treated by extracorporeal removal of IgG and immune complexes. An immunoadsorbent material for removing IgG and IgG-complexes from biological fluids is prepared by covalently binding protein A to a solid-phase silica matrix. It has been found that particularly stable, high-capacity immunoadsorbents are obtained by derivatizing the silica with amino and/or carboxyl groups, and reacting the protein A with a carbodiimide at a pH in a range from 3.5 to 4.5. Binding through free hydroxyl groups may be achieved with cyanogen halides at a pH in the range from 11.0 to 11.5. After acid washing (pH 2.0-2.5) to remove non-covalently bound protein A, the immunoadsorbent may be employed in a column for therapeutic treatment of various cancers and autoimmune disorders where IgG-complexes are implicated as suppressing factors in inhibiting a normal immune response.

41 Claims, 2 Drawing Sheets

METHOD FOR TREATMENT OF HIV-INFECTED PATIENTS

This application is a continuation-in-part of application Ser. No. 948,268, filed on Dec. 1, 1986, and now U.S. Pat. No. 4,801,449 which was a continuation-in-part of application Ser. No. 690,781, filed on Jan. 11, 1985, now U.S. Pat. No. 4,681,870.

BACKGROUND OF THE INVENTION

1. Field of the Invention

The extra corporeal treatment of blood to remove immunoglobulins and circulating immune complexes has proven useful in certain circumstances. For example, it is suspected that some cancer patients develop a particular immune complex consisting of the patient's own IgG and an antigen associated with the cancer. It is thought that such complexes can interfere with the functioning of the patient's immune system and prevent the immune system from responding to the cancer. Treatment of various cancers, including carcinomas and melanomas, using extra corporeal plasma perfusion with protein A and *Staphylococcus aureus* to remove immune complexes has yielded varying levels of success. The extra corporeal removal of IgG and immune complexes has also been beneficial in the treatment of certain immune system disorders, such as thrombotic thrombocytic purpura.

Human immunodeficiency virus-1 (HIV-1), the etiologic agent of acquired immunodeficiency syndrome (AIDS), has the property of infecting selected cells of the immune system and abrogating their function. The clinical course of HIV-1 infection often consists of a prolonged asymptomatic state, followed by severe depletion of T4+ helper lymphocytes, rendering the patient highly susceptible to opportunistic infections and neoplasms. HIV-1 infection can also cause a profound degeneration of the central nervous system. The variable course of HIV-related disease may reflect the complex life cycle of the virus now known to include both latent and lytic states in T4+ lymphocytes under the control of viral genes, as well as a state of limited replication in monocytes and macrophages.

The Centers for Disease Control estimate that there are now one to 1.5 million HIV-infected individuals in the United States who are asymptomatic. Studies of risk groups known to have been infected with HIV-1 for five or more years suggest that 30% of infected individuals will develop AIDS, that 10–15% of these individuals will develop AIDS related conditions (ARC), and that 10% of these individuals will develop chronic neurological disabilities. This translates into a projection of approximately 270,000 cumulative cases of AIDS by 1991, although some estimates run as high as 700,000 cases.

It is generally accepted that development of a vaccine is crucial to containment of the HIV-1 epidemic. However, assuming that a safe vaccine could be developed which confers immunity against all strains and types of HIV-1, it would not likely be available for 5–10 years. Moreover, it is uncertain that such a vaccine would be of any value in preventing development of AIDS in those individuals already infected with HIV-1.

Thus, even if an effective vaccine is developed, treatments to inhibit the progression of HIV-1 infection to AIDS and therapies for controlling opportunistic infections, neoplasms, and underlying HIV-1 infection will still be necessary.

Proposed strategies for treatment of HIV-1 infection include inhibition of viral replication and restoration of impaired immune function. Strategies for suppression of viral replication include development of monoclonal antibodies which block binding of virus to target cells and drugs which block reverse transcription of viral RNA, transcription of viral DNA, translation of viral mRNA, and virus assembly.

The most widely studied current therapy utilizing the DNA chain terminator azidothymidine (AZT) shows some promise, but has substantial toxicity which may limit its use. Restoration of immunity has been attempted by bone marrow transplantation and lymphocyte transfusion, by lymphokine administration, and by immunostimulatory drugs. While some reconstitution of cellular and humoral functions have been obtained with such treatments, HIV-1 infections have not been reversed and the course of AIDS has not been obviously altered.

It is somewhat paradoxical that persons with HIV-1 infection and progressive disease in fact produce neutralizing antibodies against HIV-1. The reason that these naturally-developing antibodies offer little protection is unclear although several plausible mechanisms have been suggested. First, the immunodominant regions of the viral envelope glycoprotein gp120 are known to lie outside the regions of viral attachment and penetration, and there is much variability in the immunodominant regions among different viral strains. Since multiple strains of HIV-1 are often found within a single individual, some strain selection or differentiation may occur in vivo. Additionally, much of the HIV-1 population may exist in a latent form in vivo where viral antigens are not expressed. Otherwise, adequate cell-mediated cytotoxic antibody dependent and/or complement dependent antibody mediated cytotoxic responses would be likely effective against such virus infected cells. Finally, HIV-1 infected cells may escape immune recognition by capping off their antigens.

It would therefore be desirable to develop a therapy which could provide long-term benefits for HIV-1 infected patients. The therapy should be able to restore the patient's immune activity and direct it against the intrinsic strains of HIV-1. Sustained protective immunity directed against an array of viral antigenic determinants favors successful challenge of different viral strains as they are activated from latently infected cells.

2. Description of the Relevant Art

Heat and formalin-treated *Staphylococcus aureus* Cowan I packed in a column has been employed as a therapy for neoplastic disease based on the removal of immune complexes from blood. See, e.g., Bansal et al. (1978) Cancer 42:1–18; Terman et al. (1981) N. Engl. J. Med. 305:1195–1200; Jones et al. (1980) Cancer 46:675–684; Ray et al. (1980) Cancer 45:2633–2638; Besa et al. (1981) Am. J. Med. 71:1035–1040 Holohan et al. (1982) Cancer Res. 42:3663–3668; Messerschmidt et al. (1982) Cancer Treat. Rep. 66:2027–2031; MacKintosh et al. (1983) West. J. Med. 139:36–40; Snyder et al. (1982) J. Immunol. 128:2726–2730; and Jones et al. (1984) J. Biol. Resp. Mod. 3:286–292. Terman et al. (1981) N. Engl. J. Med. 305:1195–1200 describes use of an immunoadsorbent consisting of protein A entrapped within a charcoal matrix for treatment of cancer patients. Messerschmidt et al. (1988) J. Clin. Oncol. 6:203–212 is a review of the treatment of neoplastic diseases by extra corporeal plasma perfusion. Feline leukemia virus (FeLV) infection in cats has been successfully treated by extra corporeal removal of immune complexes using *S. aureus* protein A columns. See, e.g., Jones et al. (1980) Cancer 46:675–684; Snyder et al. (1982) J. Immunol. 128:2726–2730; and Jones et al. (1984) J. Biol. Resp. Mod. 3:286–292. The treatment of autoimmune diseases by protein A plasma perfusion has been previously described. Korec et al. (1984) J. Biol. Resp. Mod. 3:330–335 and (1986) Clin. Oncology 4:210–215 describe the treatment of patients suffering from thrombotic thrombocytic purpura (an autoimmune disease) by extra corporeal removal of IgG and immune complexes in an agarose-protein A column. Nilsson et al. (1981) Blood 58:38–44 describes the extra corporeal removal of anti-factor IX antibodies using an agarose-protein A column. A portion of the experimental work reported in the present application was published in Kiprov et al. (1984) J. Biol. Resp. Mod 3:341–346 and is disclosed in grandparent U.S. Pat. No. 4,681,870. Other portions of the experimental results have been published in Messerschmidt et al. (1988) J. Clin. Oncol. 6:203–212; Kiprov et al. (1986) J. Clin. Apheresis 3:133–139; Mehta et al. (1986) Clin. Res. 34:501A; Snyder et al. (1987) Artif. Organs 11:334; and Snyder et al. (1988) Proc. IVth. International Conference on AIDS 1:194.

SUMMARY OF THE INVENTION

The present invention provides a method for the treatment of patients suffering from human immunodeficiency virus-1 (HIV-1) infection. Different stages of HIV-1 infection are treated by extra corporeal removal of free IgG and immune complexes from the patient's blood. For pre-AIDS patients, the treatment can significantly prolong the asymptomatic state prior to the development of AIDS. For patients who have already developed the clinical symptoms of AIDS, including a severely impaired immune system, the treatment can inhibit the occurrence of opportunistic secondary infections and neoplasms such as pneumonia, chronic lymphadenopathy, and diffuse, undifferentiated non-Hodgkin's lymphoma.

Extra corporeal removal of immune complexes and IgG may be achieved by withdrawing blood from the patient, separating the blood into its plasma and serum components, contacting the plasma with an immunoadsorbent specific for the IgG and immune complexes, and reinfusing the treated plasma and cellular blood components to the patient. The immunoadsorbent is preferably protein A covalently bound to an inert matrix, usually silica, but may also comprise anti-IgG or another receptor capable of specifically binding the IgG and immune complexes. The treatments are usually repeated periodically until a desired response has been achieved, or may be continued indefinitely for patients in the asymptomatic state.

DESCRIPTION OF THE SPECIFIC EMBODIMENTS

The method and system of the present invention utilize an immunoadsorbent column having an immunoadsorbent material therein which is suitable for the extra corporeal treatment of a patient's plasma to remove IgG and IgG-complexes therefrom. The extra corporeal treatment may be provided by continuously removing a patient's blood, separating the blood cells therefrom, treating the blood plasma in the immunoadsorbent column to remove the IgG and IgG-complexes, and mixing and returning the treated plasma and blood cells directly to the patient. Alternatively, after the blood has been removed and the blood cells separated, the blood cells may be directly reinfused into the patient. The separated plasma may be collected, treated in the immunoadsorbent column of the present invention, again collected and then returned to the patient at a later time.

Suitable immunoadsorbent materials comprise receptors bound to a solid phase matrix, where the receptors are capable of specifically binding immune complexes. Useful receptors include protein A, anti-Ig antibodies, C1q, and antibodies capable of binding the HIV-1 components of the immune complexes. The preferred novel immunoadsorbent material of the present invention comprises protein A covalently coupled to a solid-phase silica matrix under particular conditions which have been found to maximize activity of the protein A and binding capacity of the column while minimizing leakage of the protein A and other substances from the column during use.

Protein A is a cell surface protein which is isolated from particular strains of *Staphylococcus aureus* and able to bind free IgG and IgG-complexes. IgG-complexes are antigen-IgG complexes which circulate in patient serum and are not removed by the normal phagocytic mechanisms of the immune system. As stated above, removal of such circulating IgG-complexes is useful in the treatment of a variety of disorders, including autoimmune disorders and cancer. The immunoadsorbent material of the present invention will have a binding capacity of at least 5 mg IgG/gm adsorbent, usually 7 mg/gm or greater. The immunoadsorbent system of the present invention allows removal of up to about 750 to 1500 mg of the circulating IgG-complexes, usually about 1000 mg by treatment of the plasma.

Protein A may be obtained from cultures of *Staphylococcus aureus*, for example *S. aureus* Cowan I, by harvesting the cells and lysing with a suitable lytic agent, such as lysostaphin. The protein A may then be purified by any suitable technique, such as ion exchange combined with molecular sieve chromatography, to a final purity of 90–99%, usually about 95%. Protein A may also be obtained by expression of recombinant vectors in other bacterial hosts, as taught in U.S. Pat. No. 4,617,266, as well as by a variety of other techniques. Alternatively, suitably purified protein A may be obtained from a number of commercial suppliers, such as IMRE Corporation, Seattle, Wash.

The solid phase matrix will usually comprise inert particles, such as silica particles, glass beads, polymeric beads, agarose gels, cross-linked dextrans, and the like. Solid-phase silica matrices are preferred and may comprise virtually any form of particulate silica including amorphous silicas, such as colloidal silica, silica gels, precipitated silicas, and fumed or pyrogenic silicas; microcrystalline silicas such as diatomites; and crystalline silicas such as quartz. The silica should have a particle size in the range from about 45 to 120 mesh, usually in the range from 45 to 60 mesh.

In the preferred embodiment, the solid-phase matrix of the immunoadsorbent material will be formed from diatomite aggregates. The diatomite material will be cleaned to remove any remaining organic material and may be calcined to harden the surface of the aggregates in order to lessen breakage and degradation of the immunoadsorbent during use. The diatomite material will consist primarily of silica (silicon dioxide) with lesser amounts of other minerals, including aluminum oxide, calcium oxide, magnesium oxide, ferric oxide, and the like. Usually, the diatomite material will comprise at least 80% silica, with less than 5% by weight of any other mineral. Other impurities may be present in the diatomite, but care should be taken that such impurities are non-toxic and non-degradative to the biological fluid being treated. A particularly suitable solid-phase silica (diatomite) matrix may be obtained from Johns-Manville Corporation under the tradename Chromosorb ®.

The protein A is covalently coupled to the solid-phase silica matrix by derivatizing the matrix to introduce active reactive functional groups, and reacting the derivatized matrix with a coupling agent or under chemical conditions which binds the protein A to the matrix. Exemplary protocols for such binding are as follows.

Amino groups may be introduced to the silica matrix as the reactive functional group by any suitable method. For example, the silica matrix is first acid washed, followed by extensive rinsing with water and drying. The acid washed silica is then reacted in a 5% to 10% solution of an aminosilane, such as γ-aminopropyltriethoxysilane, with the pH adjusted to about 3.0. After 2 hours at about 75° C., the silica matrix is again washed extensively with water and dried overnight at 100° C.

Carboxyl groups may be introduced to the silica matrix as the reactive functional group by further reacting the amino-derivatized material, as just described, with succinic anhydride as follows. The silica matrix is mixed with succinic anhydride in a suitable buffer, such as 0.5M phosphate buffer, and the pH adjusted to about 6.0. After 12 to 16 hours at room temperature, the silica matrix is extensively washed, and dried.

Hydroxyl groups (in addition to those hydroxyl groups occurring in the native structure of the matrix) may be introduced to the silica matrix by any suitable method. For example, the silica matrix is first acid washed, rinsed extensively with water, and dried. The acid washed silica is then reacted in a 5-10% solution of a silane such as γ-glycidoxypropyltrimethoxysilane. After a 2 hour incubation at 75° C., the silica matrix is again washed extensively with water and dried at 100° C.

Once the silica matrix has been derivatized with either amino and/or carboxyl groups, the protein A is introduced by reaction with a carbodiimide which forms a covalent link between the matrix and the protein A. The carbodiimide will have the formula:

R'—N=C=N—R"

where R' and R" may be the same or different, being either alkyl, substituted-alkyl, benzyl, substituted-benzyl, or hydrogen. Alkyl or substituted-alkyl may be straight, branched or cyclic, and R will usually have fewer than 16 atoms other than hydrogen, more usually fewer than 12 atoms, and six or fewer heteroatoms (i.e., other than carbon and hydrogen). If substituted-benzyl, R will usually have three or fewer substitutions which will typically be halogen atoms. Suitable carbodiimides are well known in the art. The preferred carbodiimide is 1-cyclohexyl-3-(2-morpholinoethyl)carbodiimide metho-p-toluenesulfonate.

The binding reaction for the amino-derivatized matrix is carried out under the following conditions. The protein A is mixed in water in the presence of the carbodiimide. The pH of the solution is adjusted to the range from 3.5 to 5.0, usually about 4.5, and the silica matrix is introduced and gently mixed for an extended period, usually about 15 to 30 hours, more usually about 20 to 25 hours at room temperature. The matrix is then extensively washed with water, dried, and acid washed at a pH from about 2.0 to 2.5, usually about 2.25, to remove labile protein and other substances which are non-covalently bound to the silica matrix. The material is then finally washed, dried and checked for the presence of pyrogens. A suitable test for the presence of pyrogens is the limulus ambeocyte lysate (LAL) test, commercially available as a kit from Marine Biologicals, Inc., P.O. Box 546, Marmora, N.J. 08222.

The binding process for the carboxyl-derivatized silica matrix is as follows. A carbodiimide (as above) is dissolved in water, and the solution is adjusted to a pH in the range from 3.5 to 4.5, usually about 3.5 pH. After introducing the silica matrix, the solution is gently mixed for an extended period, usually about 10 to 25 hours, more usually about 12 to 20 hours, at room temperature. The silica matrix is then removed and extensively washed with water. The protein A is then dissolved in water, the pH adjusted to the range from 3.5 to 5.0, usually about 4.5, and the silica matrix added and mixed for about 15 to 30 hours, usually about 20 to 25 hours at room temperature. The silica matrix is then extensively washed with water, dried, and washed one time in an acid wash (pH 2.0 to 2.5, usually about 2.25) to remove non-covalently bound protein A and other substances. The silica matrix is then washed a final time, and checked for pyrogens.

The binding process for the hydroxyl derivatized silica matrix is as follows. Cyanogen bromide is dissolved in water. The silica matrix is added to water and the pH is adjusted to 11.0. The cyanogen bromide solution is added to the silica matrix, the mixture is constantly stirred keeping the silica particles in suspension, and the pH is maintained between 11.0 and 11.5 by addition of NaOH until pH stabilization occurs. The activated silica matrix is extensively washed with water, mixed with a solution of protein A with the pH adjusted to 8.5-9.0, and mixed overnight at 25° C. After coupling, the matrix is washed extensively with water, dried, and washed one time in an acid wash, pH 2.5, to remove non-covalently bound and acid labile protein A linkages. The silica matrix is washed a final time and checked for pyrogens.

As demonstrated in the Experimental section hereinafter, the pH range of from 3.5 to 4.5 for binding of the protein A to the amino and/or carboxyl functional groups on the silica matrix is critical. Similarly, the binding of the protein A to the hydroxyl functional groups at a pH in the range from 8.5 to 9.0 is also critical. The efficiency of binding and the retained activity of the protein A both diminish as the pH deviates outside of these narrow ranges. Moreover, it has been found that a mild acid wash with a pH in the range from about 2.0 to 2.5 successfully removes non-covalently bound substances from the silica matrix, particularly cleaving labile protein A linkages. The acid treatment is thus important in achieving a stable immunoadsorbent material which is able to retain the IgG and IgG-complexes bound within the column and avoid loss of protein A into the serum being treated.

Figure 1:
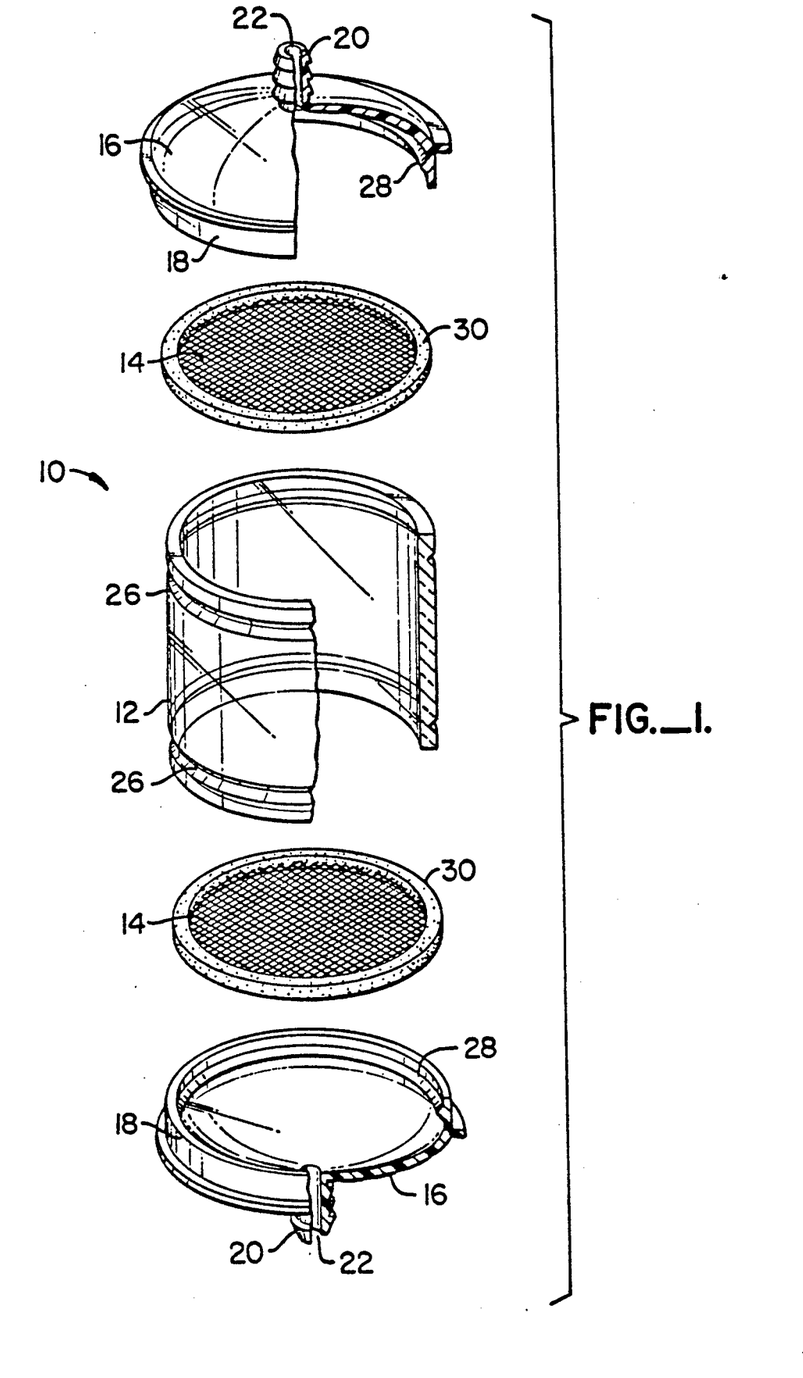
FIG. 1 is an exploded view of the immunoadsorbent column of the present invention.

Referring now to FIG. 1, the construction of a suitable cartridge 10 for containing the immunoadsorbent material as just described is illustrated. The cartridge 10 comprises a cylinder 12, a pair of retaining screens 14, and a pair of end caps 16. The end caps 16 each include a flange element 18 projecting from one surface thereof and a connector nipple 20 projecting from the other surface thereof. The connector nipple includes an axial passage 22 therethrough to define inlet/outlet ports through the end caps 16.

The cylinder 12 includes an annular groove 26 at each end thereof. The flange element 18 on each end cap includes a mating ring 28 on the inner cylindrical surface thereof, which mating ring engages the annular groove 26 when the caps are placed over the end of the cylinder 12. Each screen 14 includes a gasket 30 around its circumference, which gasket serves as a sealing member between the end cap 16 and the cylinder 12 when the cartridge 10 is assembled. To assemble the cartridge 10, a first screen 14 is placed over one end of the cylinder 12, and an end cap 16 is fitted over the screen 14. The cylinder 12 is then filled with the immunoadsorbent material as described above, and assembly of the cartridge completed by placing the remaining screen 14 and end cap 16 in place.

The dimensions of the cartridge 10 are not critical, and will depend on the desired volume of immunoadsorbent material. The volume of the cylinder 12 will typically range from about 50 to 500 cc, having a diameter in the range from about 4 to 8 cm and a length in the range from about 5 to 10 cm.

Figure 2:
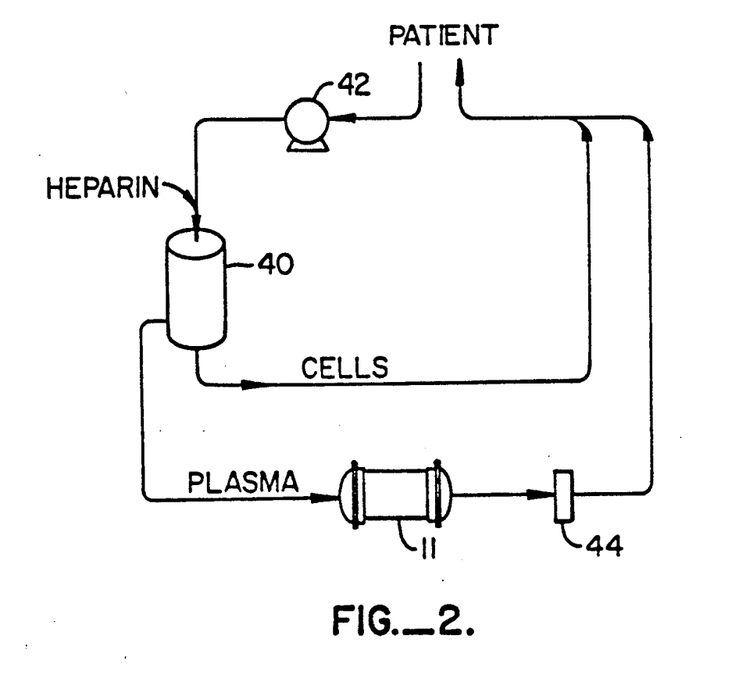
FIG. 2 is a diagrammatic representation of a system for the extra corporeal treatment of blood constructed according to the present invention.

A column 11 (FIG. 2) which comprises a cartridge 10 containing a suitable amount of the immunoadsorbent material prepared as described above, may be sterilized, typically with a gas sterilant such as ethylene oxide, and either used immediately or sealed and stored for later use.

Treatment protocols may be performed with the column 11 as follows. Prior to use, the column 11 will be washed with normal saline followed by a wash with normal saline containing heparin or other suitable anticoagulant such as anti-coagulant citrate dextrose (ACD). The column 11 may then be connected to a cell separator 40 (FIG. 2) to receive separated plasma therefrom. The cell separator 40 may be a continuous flow cell separator, such as an IBM Model 2997, available from COBE, Golden, Colorado, or may comprise a semi-permeable membrane which allows passage of the plasma and blood proteins, but prevents passage of the cellular elements of the blood. In the case of a semipermeable membrane, a blood pump 42 will be required to pass the blood through the membrane. Suitable blood pumps include a tube and peristaltic pumps where the blood is isolated from the pumping machinery to prevent contamination. The blood will pass through the cell separator 40 at a rate in the range from about 10 to 20 ml/min typically until a total volume of about 2 liters of blood has been passed. The blood cells are mixed with the plasma passing from the treatment column 11, and the recombined blood returned to the patient. Typically, a microfilter 44 is provided at the outlet of the treatment column 11 to prevent passage of macroscopic particles which might be lost from the column 11.

Individual treatment protocols employing the immunoadsorbent column of the present invention may be performed by an on-line (continuous) protocol where a patient's blood is continuously drawn and separated into plasma and cellular components. While the blood is continuing to be drawn, the plasma is contacted with the immunoadsorbent and the plasma and cellular components are reinfused into the patient. Such an on-line protocol allows relatively large volumes of plasma in the range from about 300 to 3000 ml to be treated.

Alternatively, off-line (discontinuous) treatment protocols may also be employed where a discrete volume of blood is drawn, usually in the range from about 200 to 600 ml, by conventional phlebotomy. The blood is then separated into plasma and cellular components, and then cellular components substantially immediately reinfused into the patient. The plasma is separately treated with the immunoadsorbent and reinfused to the patient some time later, usually from several hours to several days later. Multiple volumes of blood, e.g., two, three, or four volumes within the above range, may be treated at any one session, with the cellular components and treated plasma being returned to the patient prior to drawing the next blood volume.

The method of the present invention is effective in treating HIV-1 infected individuals both before and after the development of AIDS. For HIV-1 infected patients free from clinical signs of AIDS (e.g., T4+ cell reduction), the treatment is intended to postpone or delay the onset of AIDS beyond the time when such progression of the disease might otherwise be expected. Under the best circumstances, the onset of clinically-defined AIDS will be delayed indefinitely.

Treatment of pre-AIDS patients will usually consist of individual treatment protocols (as described above) which are repeated periodically, usually at a frequency of from about 1 to 4 per week, more usually at about 2 to 3 per week. Treatment at such frequency may be continued indefinitely, or treatment may consist of a discrete number of treatments, for example in the range from 24 to 36.

Treatment of AIDS patients is intended as a prophylactic or therapeutic treatment of opportunistic secondary infections and neoplasms which are prevalent in AIDS patients. Common infections include pneumonia, particularly a rare form of pneumonia caused by the protozoan *Pneumocystis carinii*, chronic lymphadenopathy, and the like. Common neoplasms include Kaposi's sarcoma and diffuse, undifferentiated non-Hodgkin's lymphoma. Other conditions benefited include central nervous system degeneration.

Treatment of patients having clinically-defined AIDS (usually characterized by HIV-1 infection coupled with T4+ lymphocyte depletion) but free from secondary infections and neoplasms will usually be treated periodically until at least a partial restoration of immune function is restored. Individual treatment protocols will then be continued, but usually at a lesser frequency. The initial treatment protocols will usually be performed at a frequency in the range from about 1 to 4 per week, more usually from about 2 to 3 per week, for a time period of at least 12 weeks or until restoration of the immune function is observed. Maintenance treatment will then be continued at a frequency of from 1 to 3 per week, more usually about 1 to 2, for an indefinite period.

Treatment of patients suffering from secondary infections or neoplasms will usually be more aggressive, with a frequency in the range from 3 to 5 per week until at least a partial response or remission is observed. Maintenance treatment will then be continued at a frequency of from 1 to 3 per week, more usually about 2 to 3 per week, for an indefinite period.

The present invention further comprises systems including immunoadsorbent columns, as described above, in combination with instructions or package inserts which describe the treatment protocol, just set forth. The instructions will further set forth that the treatment protocols are indicated for patients suffering from the various stages of HIV-1 infection, as set forth above.

The following examples are offered by way of illustration and not by way of limitation.

EXPERIMENTAL

1. Preparation of Immunoadsorbent Material

Acid washed silica matrix (Chromosorb® P, No. C5889, Johns-Manville, 1.25 kilograms) was weighed out, divided into 4 parts, and added to four Fernback type flasks. The matrix was re-hydrated with water and vigorously shaken overnight in a gyrotary shaker at approximately 150 rpm. After this procedure, the silica matrix was extensively washed with water to remove generated fine particles. This procedure appeared to make the shape of the silica matrix particles more uniform resulting in matrix particles which generate few fines in later handling procedures. After washing, the silica matrix was added to an approximately 5–10% solution of appropriate silane, incubated for 2 hours at 75° C., extensively washed with water, and baked dry at 115° C.

The dried silanized silica matrix (1 kilogram) was re-hydrated and extensively washed with water to remove generated fines. The silica matrix was then mixed with 2 grams of protein A and 50 grams of carbodiimide (1-cyclohexyl-3-(2-morpholinoethyl) carbodiimide metho-p-toluenesulfonate) and the pH of the mixture adjusted to 4.5.

The mixture was gently rotated on a roller apparatus for 22 hours at 25° C. The silica matrix was then extensively washed with water, dried at 37° C., and the uptake of protein A was determined. After drying, 3 liters of acid water, pH 2.5, was added to the silica matrix, incubated for 5 minutes at 25° C., and the amount of protein A released from the matrix was determined. The matrix was extensively washed with water, dried, and the amount of protein A per gram of silica was determined. The results were as follows:

| Bound Protein A | 1966 mg |
| Protein A released | 440 mg |
| Protein A/gm adsorbent | 1.5 mg |

2. Use of Immunoadsorbent to Separate IgG and IgG Complexes from Normal Human serum Immunoadsorbent prepared as described above was incubated with 2 ml of normal human serum for 5 minutes at 25° C. After incubation, the silica matrix was washed with 100 ml of phosphate buffered saline (PBS), pH 7.5. Bound proteins were eluted with 12.5 ml of PBS, pH 2.5, and neutralized to pH 7.5. The total protein eluted was determined to be approximately 10 mg, using the procedure as described by Lowry et al. (1951) J. Biol. Chem. 193:265–272. The eluted protein was subjected to polyacrylamide gel electrophoresis, and prominent bands were detected at 50 kD and 25 kD, corresponding to the heavy and light chains of IgG, respectively. The presence of IgG was confirmed by double immunodiffusion analysis employing γ-chain specific anti-human IgG.

To determine removal of IgG complexes by the immunoadsorbent, 2.5 ml of normal human serum was incubated with heat-aggregated human IgG to fix complement to the aggregates. This combination behaves as immune complexed IgG. Immunoadsorbent prepared as described above was incubated with 0.8 ml of the heat-aggregated serum for 5 minutes at 25° C. This was repeated 3 times until a total volume of 2.4 ml was passed through the immunoadsorbent, and fractions were collected until all the serum was passed through the immunoadsorbent. IgG immune complexes in pre- and post-perfusion serum fractions were measured employing the Raji cell binding IgG immune complex assay as described by Theofilopoulos et al. (1974) J. Exp. Med. 140:1230–1244. The results are presented in Table 1.

TABLE 1

| Sample* | Immune Complex (μg/ml) | % Reduction |
|---|---|---|
| Pre-perfusion | 160 | — |
| Post-perfusion - | | |
| Fraction 1 | 120 | 25 |
| Fraction 2 | 125 | 22 |
| Fraction 3 | 105 | 34 |
| Fraction 4 | 104 | 35 |

*Equivalent protein quantities were assayed to control for dilutional effects.

As shown in Table 1, immune complex levels of the serum were reduced by passage through the immunoadsorbent.

3. Therapeutic Use of Column to Treat Kaposi's Sarcoma and Thrombocytopenia HIV-Infected Patients Twenty-three HIV-infected patients with AIDS and Kaposi's sarcoma were treated by extra corporeal immunoadsorption using protein A columns as described above an average of three times per week for four weeks. An increase in white cell count occurred five hours after the first procedure, and its magnitude varied from 3–10 times the initial value. During the first week of treatment, the increase was primarily due to granulocytes, while approximately one week later, lymphocytes predominated. At that time, increased blastogenic response to mitogens was observed along with an increase in the T4+/T8+ cell ratio. Increased NK cell activity was also observed at that time.

Grossly identifiable changes in Kaposi's sarcoma lesions started to occur during the first or second week of treatment in all responding patients. No new lesions appeared while patients were being treated. A reddish halo developed around 40–50% of existing lesions. Between 20–30% of lesions showed slight decreases in size along with central umbilication. Approximately 10% of the lesions disappeared completely. Of the 17 patients evaluable for response, six patients exhibited partial responses against Kaposi's sarcoma, two patients exhibited minor responses, eight patients exhibited stabilization of disease, one patient exhibited progression of disease. Responses were obtained in patients with stage I, II, and IV disease.

Twenty-nine patients with HIV-infection and thrombocytopenia were also treated by extra corporeal immunoadsorption using PROSORBA columns an average of six times over a five week period. In 16 patients, platelet-directed IgG and CIC were decreased significantly. Treatment was associated with immune modulation leading to stimulation of an anti-F(ab')$^2$ antibody response. The antibody functioned by binding to both platelet-directed IgG and CIC, neutralizing their binding capacity for platelets and enhancing their clearance from the circulation. This clearance was associated with significant normalization of platelet counts in those patients from pre-treatment levels of 46,438±6,342/mm$^3$ to peak levels of 102,125±12,399/mm$^3$ 103 weeks after completion of the treatment (P<0.01). Twelve patients sustained elevated platelet counts over a mean follow-up period of eight months at last evaluation without any other treatment.

Levels of HIV p24 antigen in patient sera were quantitated using the ELISA test kit obtained from DuPont (Table 2). Sufficient material for this analysis was available from 12 patients with AIDS/Kaposi's sarcoma (AIDS/KS) and from 13 patients with HIV-associated ITP (HIV-ITP). Seven patients with AIDS/KS and five patients with HIV-ITP had detectable levels of circulating HIV p24 which averaged (x±standard error) 79±16 pg/ml for AIDS/KS patients (range 24–128 pg/ml) and 100±32 pg/ml for the five HIV-ITP patients (range 31–181 pg/ml). During treatment, 3 of 7 AIDS/KS patients and 3 of 5 HIV-ITP patients experienced reduction in levels of circulating HIV p24. The amounts of reduction of p24 ranged from 17–100% in the case of AIDS/KS patients to 17–35% in the HIV-ITP patients.

TABLE 2

| Patient No. | p24 (pg/ml) Pre Rx | Post Rx | Change | Clinical Response |
|---|---|---|---|---|
| AIDS/KS | | | | |
| 81[1] | 48 | 54 | ↑ 13% | <PR[3] |
| 97 | 120 | 55 | ↓ 54% | <PR |
| 126 | 121 | 341 | ↑ 182% | NE |
| 129 | 69 | 57 | ↓ 17% | P |
| 135 | 128 | 135 | ↑ 5% | P |
| 138 | 24 | <10 | ↓ 100% | S |
| 146 | 43 | 48 | ↑ 12% | S |
| HIV-ITP | | | | |
| 5[2] | 31 | 20 | ↓ 35% | NR[4] |
| 17 | 174 | 176 | ↑ 1% | R |
| 26 | 74 | 109 | ↑ 20% | R |
| 30 | 181 | 151 | ↓ 17% | R |
| 35 | 41 | 33 | ↓ 20% | R |

[1]Patients received an average of three treatments per week for four weeks.
[2]Patients received one treatment per week for four weeks.
[3]PR = Partial response = >50% reduction in tumor size and appearance of no new metastatic lesions.
<PR = Less than partial response = >25% reduction in tumor size but <50% reduction and appearance of no new metastatic lesions.
S = Stable = Less than 25% reduction or increase in tumor size and appearance of no new metastatic lesions.
P = Progression = >25% increase in tumor size and/or appearance of new metastatic lesions.
NE = Not evaluable.
[4]R = Response posttreatment.
For patients with platelet counts <50,000/mm$^3$, Response = 100% increase in platelet counts.
For patients with pretreatment platelet counts of >50,000/mm$^3$, Response = 50% increase in platelet counts.
NR = no response posttreatment.

Levels of antibody to HIV p24 in patient sera were quantitated using the ELISA test kit available from DuPont (Table 3). Sera from 14 patients with AIDS/KS and 13 patients with HIV-ITP were evaluated. Briefly, sera were diluted 1:2,000–1:200,000 with buffer provided by the manufacturer prior to analysis. The slopes of titration curves of optical density (OD) by ELISA and serum dilution were determined by regression analysis. Correlation coefficients were uniformly >0.95. Titers were defined as the calculated dilution of serum which yielded an OD reading equal to the cutoff value for positivity in the assay as per the manufacturer's protocol. During treatment 11 of 14 AIDS/KS patients and 10 of 13 HIV-ITP patients showed increases in titer of p24 antibody. The increases ranged from 6–227% in the case of AIDS/KS patients and from 3–205% in the case of HIV-ITP patients.

TABLE 3

| Patient No. | Titer of Anti p24 (dilution −1) Pre Rx | Post Rx | Change | Clinical Response |
|---|---|---|---|---|
| AIDS/KS | | | | |
| 3 | 17,800 | 26,220 | ↑ 47% | PR |
| 21 | 39,520 | 38,690 | ↓ 2% | PR |
| 62 | 4,130 | 6,648 | ↑ 61% | PR |
| 81 | 6,023 | 7,096 | ↑ 18% | PR |
| 97 | 13,460 | 14,221 | ↑ 6% | PR |
| 99 | 10,300 | 9,093 | ↓ 13% | <PR |
| 123 | 6,781 | 8,221 | ↑ 21% | <PR |
| 126 | 16,960 | 28,380 | ↑ 67% | NE |
| 129 | 11,130 | 16,980 | ↑ 53% | P |
| 135 | 23,140 | 57,060 | ↑ 147% | P |
| 138 | 13,000 | 9,863 | ↓ 32% | S |
| 146 | 58,200 | 190,100 | ↑ 227% | S |
| 147 | 6,205 | 16,320 | ↑ 163% | P |
| 148 | 43,500 | 61,000 | ↑ 40% | P |
| HIV/ITP | | | | |
| 3 | 16,960 | 28,380 | ↑ 67% | R |
| 4 | 25,560 | 77,850 | ↑ 205% | R |
| 5 | 27,050 | 26,850 | ↓ 1% | NR |
| 8 | 8,217 | 8,780 | ↑ 7% | R |
| 12 | 17,070 | 31,340 | ↑ 84% | R |
| 14 | 30,140 | 34,040 | ↑ 13% | R |
| 15 | 8,764 | 9,018 | ↑ 3% | NR |
| 16 | 124,000 | 80,910 | ↓ 53% | R |
| 17 | 12,230 | 15,410 | ↑ 26% | R |
| 26 | 7,814 | 18,370 | ↑ 135% | R |
| 27 | 19,600 | 52,000 | ↓ 165% | NR |
| 30 | 32,040 | 27,780 | ↓ 15% | R |
| 35 | 4,437 | 6,400 | ↑ 44% | NR |

Rx = treatment

These experiments demonstrated that one can achieve an increase in antiviral antibody and a decrease in viral protein levels in some patients following extra corporeal immunoadsorption to remove molecules such as immune complexes and IgG. The treatment of HIV-infected patients was accomplished with transient and easily managed side effects, predominantly fever and chills. The results indicate that some AIDS-associated conditions respond favorably to extra corporeal immunoadsorption therapy and that responses may be obtained without serious side effects.

Although the foregoing invention has been described in detail for purposes of clarity of understanding, it will be obvious that certain modifications may be practiced within the scope of the appended claims.

What is claimed is:

1. A method for treating a patient infected with human immunodeficiency virus-1 (HIV-1), said method comprising:
    extracorporeally contacting the patient's plasma with an immunoadsorbent material capable of binding immune complexes, and
    reinfusing the treated plasma to said patient.

2. A method as in claim 1, wherein the immunoadsorbent comprises protein A covalently bound to an inert matrix.

3. A method as in claim 1, wherein the treatment protocol for contacting the patient's plasma comprises:
drawing a preselected volume of blood from the patient;
separating the plasma from the cellular components of the blood;
reinfusing the cellular components to the patient; and
reinfusing the treated plasma to the patient.

4. A method as in claim 3, wherein the cellular components and treated plasma are recombined and reinfused while the predetermined volume of blood is still being drawn.

5. A method as in claim 3, wherein the cellular components are reinfused substantially immediately after separation while the plasma is reinfused after the entire volume of blood has been drawn.

6. A method as in claim 4, wherein the predetermined volume of blood is sufficient to provide a plasma volume in the range from about 300 to 3000 ml.

7. A method as in claim 5, wherein the predetermined volume of blood is in the range from about 200 to 600 ml.

8. A method as in claim 3, wherein the treatment protocol is repeated with a frequency of at least about once per week.

9. A method as in claim 3, wherein the treatment protocol is repeated indefinitely.

10. A method as in claim 3, wherein the treatment protocol is repeated over a time period in the range from about 8 to 12 weeks.

11. A method for inhibiting the development of acquired immunodeficiency syndrome (AIDS) in patients infected with human immunodeficiency virus-1 (HIV-1), said method comprising:
extracorporeally contacting the plasma of a patient who is asymptomatic of AIDS with an immunoadsorbent material capable of binding immune complexes, and
reinfusing the treated plasma to said patient.

12. A method as in claim 11, wherein the immunoadsorbent comprises protein A covalently bound to an inert matrix.

13. A method as in claim 11, wherein the treatment protocol for contacting the patient's plasma comprises:
drawing a preselected volume of blood from the patient;
separating the plasma from the cellular components of the blood;
reinfusing the cellular components to the patient; and
reinfusing the treated plasma to the patient.

14. A method as in claim 13, wherein the cellular components and treated plasma are recombined and reinfused while the predetermined volume of blood is still being drawn.

15. A method as in claim 13, wherein the cellular components are reinfused substantially immediately after separation while the plasma is reinfused after the entire volume of blood has been drawn.

16. A method as in claim 14, wherein the predetermined volume of blood is sufficient to provide a plasma volume in the range from about 300 to 3000 ml.

17. A method as in claim 15, wherein the predetermined volume of blood is in the range from about 200 to 600 ml.

18. A method as in claim 13, wherein the treatment protocol is repeated with a frequency of at least about once per week.

19. A method as in claim 13, wherein the treatment protocol is repeated indefinitely.

20. A method as in claim 13, wherein the treatment protocol is repeated over a time period in the range from about 8 to 12 weeks.

21. A method for treating patients suffering from acquired immunodeficiency syndrome (AIDS), said method comprising:
extracorporeally contacting the plasma of a patient who is diagnosed as having a secondary infection or neoplasm other than Kaposi's sarcoma associated with AIDS with an immunoadsorbent material capable of binding immune complexes, and
reinfusing the treated plasma to said patient.

22. A method as in claim 21, wherein the immunoadsorbent comprises protein A covalently bound to inert matrix.

23. A method as in claim 21, wherein the treatment protocol for contacting the patient's plasma comprises:
drawing a preselected volume of blood from the patient;
separating the plasma from the cellular components of the blood;
reinfusing the cellular components to the patient; and
reinfusing the treated plasma to the patient.

24. A method as in claim 23, wherein the cellular components and treated plasma are recombined and reinfused while the predetermined volume of blood is still being drawn.

25. A method as in claim 23, wherein the cellular components are reinfused substantially immediately after separation while the plasma is reinfused after the entire volume of blood has been drawn.

26. A method as in claim 24, wherein the predetermined volume of blood is sufficient to provide a plasma volume in the range from about 300 to 3000 ml.

27. A method as in claim 25, wherein the predetermined volume of blood is in the range from about 200 to 600 ml.

28. A method as in claim 23, wherein the treatment protocol is repeated with a frequency of at least about once per week.

29. A method as in claim 23, wherein the treatment protocol is repeated indefinitely.

30. A method as in claim 23, wherein the treatment protocol is repeated over a time period in the range from about 8 to 12 weeks.

31. A system for treating patients infected with human immunodeficiency virus-1 (HIV-1), said system comprising:
an immunoadsorbent column containing a material capable of specifically binding immune complexes in a patient's plasma which is contacted with the material; and
instructions comprising a protocol for the use of the column for treating patients infected with HIV-1 by extracorporeally contacting the patient's plasma to remove immune complexes and that the treated plasma is to be returned to the patient.

32. A system as in claim 31, wherein the immunoadsorbent column comprises protein A covalently bound to an inert matrix.

33. A system as in claim 31, wherein the column contains from 100 mg to 1000 mg of protein A.

34. A system as in claim 31, wherein the instructions describe that the plasma is to be contacted according to the following treatment protocol:

drawing a preselected volume of blood from the patient;

separating the plasma from the cellular component of the blood;

reinfusing the cellular component to the patient; and reinfusing the plasma to the patient.

35. A system as in claim 34, wherein the instructions set forth that cellular components and the treated plasma are recombined and reinfused while the predetermined volume of blood is still being drawn.

36. A system as in claim 34, wherein the instructions set forth that cellular components are reinfused substantially immediately after separation while the plasma is reinfused after the entire volume of blood has been drawn.

37. A system as in claim 35, wherein the instructions set forth that the predetermined volume of blood is sufficient to provide a plasma volume in the range from about 300 to 3000 ml.

38. A system as in claim 36, wherein the instructions set forth that the predetermined volume of blood is in the range from about 200 to 600 ml.

39. A system as in claim 34, wherein the instructions set forth that the treatment protocol is repeated with a frequency of at least about once per week.

40. A system as in claim 34, wherein the instructions set forth that the treatment protocol is repeated indefinitely.

41. A method as in claim 34, wherein the instructions set forth that the treatment protocol is repeated over a time period in the range from about 8 to 12 weeks.

* * * * *